United States Patent
Rastegar

[19]

[11] Patent Number: 6,138,501
[45] Date of Patent: Oct. 31, 2000

[54] PLUNGER BAR

[75] Inventor: Jahangir Rastegar, Stony Brook, N.Y.

[73] Assignee: KeySpan Corporation, Hicksville, N.Y.

[21] Appl. No.: 09/174,017

[22] Filed: Oct. 16, 1998

Related U.S. Application Data

[60] Provisional application No. 60/062,232, Oct. 16, 1997.
[51] Int. Cl.$^7$ ........................................................ G01N 3/42
[52] U.S. Cl. ................................................. 73/82; 73/12.09
[58] Field of Search .............................. 73/11.01, 12.01, 73/12.07, 12.09, 81, 82, 85

[56] References Cited

U.S. PATENT DOCUMENTS

| | | | |
|---|---|---|---|
| 4,470,293 | 9/1984 | Redmon | 73/12.09 |
| 5,134,280 | 7/1992 | Johnston et al. | 250/227.11 |
| 5,347,851 | 9/1994 | Grudzien, Jr. et al. | 73/53.01 |
| 5,416,428 | 5/1995 | Swart | 324/759 |

*Primary Examiner*—Max Noori
*Attorney, Agent, or Firm*—Dilworth & Barrese

[57] ABSTRACT

A plunger apparatus is presently disclosed that includes a housing, and a probe slidably supported by the housing. A damping assembly is supported by the housing and cooperating with the probe. The housing, preferably, has a proximal portion and a distal portion wherein the probe is slidably mounted within the housing and extending axially from the distal portion. The probe, desirably, has an increased diameter portion at a proximal end thereof and a penetrating tip adjacent a distal end thereof. A hammer mechanism is provided that is slidably supported by the housing and cooperatively engaging the probe and cooperating with the damping assembly. The housing may also include a handle assembly. A method for using the plunger apparatus is also disclosed.

17 Claims, 5 Drawing Sheets

PLUNGER BAR

This application claims the benefit of U.S. Provisional No. 60/062,232 filed Oct. 16, 1997.

BACKGROUND

1. Technical Field

The present disclosure relates generally to an apparatus and method for a manually operated plunger bar for creating holes. In particular, the plunger bar is designed to attenuate transmitted shock forces between the tool and the operator.

2. Description of Related Art

Plunger bars are used to create holes in soil, concrete, etc. The most common users are gas utility personnel which use the devices to make holes in the ground or between cracks in pavement in order to insert a gas detection sniffer and locate possible gas leaks. The prior art plunger bar is a manually operated device, designed to be portable and stowable on a service truck for use at remote locations.

FIG. 1 shows an assembly of the prior art plunger bar 10. The plunger bar is generally used in a substantially vertical orientation. The plunger bar comprises a handle 26 which has a piston 18 and a barrel 16. The barrel 16 is free to slide down the length of the piston 18 and the barrel's motion is halted upon impact with a flange 20 located at the lower end of the piston 18. The barrel 16 envelopes the piston 18 when the barrel is in the down position. The barrel has a hammer 14 attached at its lower end which is consequently also the point of impact with the flange 20 when the plunger bar 10 is in use. The hammer supplies extra weight to the barrel 16 hence increasing the impact load when impacting the flange 20. On the end of piston 18 opposite the barrel 16, there is a probe 30 which comprises a solid rod 22 fixedly attached to the piston 18 and a removable conical tip 28 at the free end. The tip 28 can therefore be replaced if damaged. The removable tip 28 is generally sized 3/16 inches to 1/4 inches larger than the diameter of the rod 22. This is to reduce the friction on the rod when a portion of the rod is buried during use.

The barrel 16 is raised by an operator to a maximum height as defined by the hammer 14 and a flange 12 on the end of the piston 18 opposite the probe 30. At this point the operator accelerates the barrel 16 by releasing it or driving it downward. The downward velocity of the barrel 16 and hammer 14 increases until impact. The combined mass of the barrel 16 and hammer 14 multiplied by the velocity at impact gives the momentum imparted to the flange 20 thereby forcing the probe 30 with the removable conical tip 28 into the ground. The penetration of the rod into the ground is achieved when the impulsive impact force of the barrel 16 and hammer 14 overcome the soil resistance force. After the impact, the hammer 14 and barrel 16 recoils and loses contact with flange 20, and the probe 30 is driven further into the ground.

An operator is responsible for securing the plunger bar 10 upright during its operation. The operator also provides the necessary energy to the barrel 16 by lifting it and forcing it downward. In order to be able to complete both activities, it is necessary for the operator to hold the barrel 16 through the impact. This presents some difficulty when harder soils, rocks, concrete, etc. are encountered. Softer soils damp out harmful vibrations, but when a very high resistance is encountered the vibrations due to impacts are no longer damped and are transferred through the plunger bar 10 into the operator. In very high resistance media, the probe 30 cannot penetrate, and this reduces the impact time to a minimum forcing the operator to experience the maximum impact force.

The impact forces transferred to the operator can cause injury. Immediate damage is possible due to stresses imparted to the arms and wrists of the operator. Also fatigue injuries are common over time or with repetitive use of the plunger bar 10. Therefore, a need exists for a plunger bar that reduces stresses imparted to operators by reducing the impact loads during operation.

SUMMARY

An object of the present disclosure is to provide a plunger bar which reduces fatigue and stress to an operator resulting from an impact force, and also increases the penetration force of the probe.

The present apparatus comprises a plunger bar including a probe which is driven into the ground by manually forcing it downward, whereby the driving effect is supplemented by the provision of a hammer enclosed within a slidably moving barrel within the plunger bar housing. Impacts which are potentially harmful to the human operators, created by shock waves that cause stress in the operator's arms and wrists, are attenuated in the plunger bar through the use of a spring-damper arrangement located within the housing. Thus, a plunger bar is disclosed which reduces the hazards to the human operator. Furthermore, the spring-damper arrangement advantageously enhances the penetration force of the probe.

A plunger apparatus is disclosed that includes a housing, a probe slidably supported by the housing, a hammer mechanism slidably supported by the housing and cooperatively engaging the probe to distally advance the probe into the surface, and a damping assembly supported by the housing that includes at least one energy absorbing member and cooperates with the hammer mechanism to attenuate impact forces generated during operation of the apparatus. Desirably, the damping assembly is positioned to generate a recoil force for cooperating with the hammer mechanism to increase impact forces for driving the probe into a surface. Most desirably, the at least one energy absorbing member includes a spring assembly. Preferably, the probe has an increased diameter portion to retain the probe within the housing.

In a preferred embodiment, the hammer mechanism includes an anvil having a top and a bottom surface, the bottom surface cooperatively engaging the probe for its advance into a surface. In this embodiment, the hammer mechanism also includes a cylinder attached t6 the anvil that defines a channel for slidable receipt and support of the probe. An end cap is mounted to the cylinder which provides a movable limit for the probe.

In another preferred embodiment, the damping assembly includes a second energy absorbing member cooperating with the first energy absorbing member. Both energy absorbing members being in operative engagement with the hammer mechanism to attenuate impact forces generated during operation of the apparatus. Further, the second energy absorbing member generates a recoil force to increase the impact forces. Preferably, the first energy absorbing member is slidably supported about the cylinder and cooperates with the bottom surface of the anvil and the second energy absorbing member is also slidably supported about the cylinder and cooperates with the end cap. Desirably, the second energy absorbing member generates the recoil force.

In yet another preferred embodiment, the damping assembly includes a bumper member fixedly attached adjacent a proximal portion of the housing.

In another preferred embodiment, the housing includes a handle assembly. Preferably, the handle assembly includes a first handle portion and a second handle portion, each portion extending from the housing and defining an open region therebetween.

In a most preferred embodiment, the plunger apparatus includes a housing having a proximal portion and a distal portion and the housing further defines a channel. An elongated probe is also included that is slidably mounted within the housing and axially extending from the distal portion of the housing. A hammer mechanism is included that is cooperatively engageable with a proximal end of the elongated probe. The hammer mechanism includes an anvil and a cylinder mounted within the housing. The cylinder defines a channel for supporting the probe therewithin and the anvil is slidably movable within the housing and into engagement with the probe. A spring assembly is mounted within the housing and slidable about the cylinder and engageable with the anvil, the spring assembly being operatively associated with the hammer mechanism. Preferably, the elongated probe has an increased diameter portion to retain the probe within the housing.

A method is disclosed for detecting gas leaks, including the steps of positioning a plunger adjacent to a gas line, the plunger including, a housing, a probe, a hammer, and a damping assembly, raising the housing of the plunger to a desired height over a surface, and lowering the housing to accelerate the hammer to impact the probe towards and into the surface for detecting a gas leak.

BRIEF DESCRIPTION OF DRAWINGS

The present device will be described in detail in the following description of preferred embodiments with reference to the following figures wherein.

DETAILED DESCRIPTION OF PREFERRED EMBODIMENTS

The preferred embodiment(s) of the method and apparatus disclosed herein are discussed in terms of penetrating procedure and devices for making holes in soil, concentrate and the like. It is further envisioned that such apparatus may be used for detecting sub-surface objects, for example, in the detection of gas leaks by utility personnel.

Figure 1:
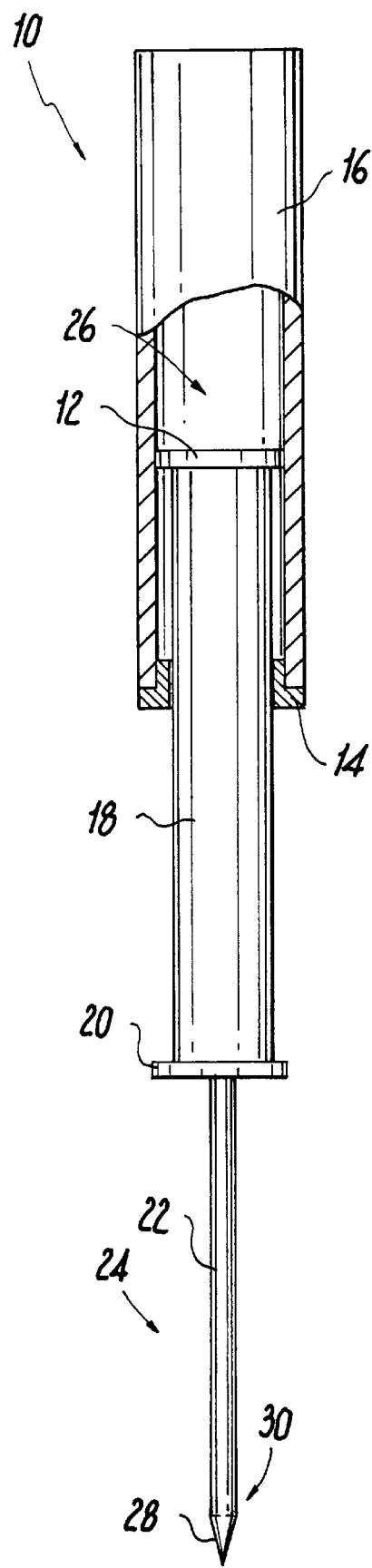
FIG. 1 is a side view in cross-section of a plunger bar in accordance with the prior art.
Figure 2:
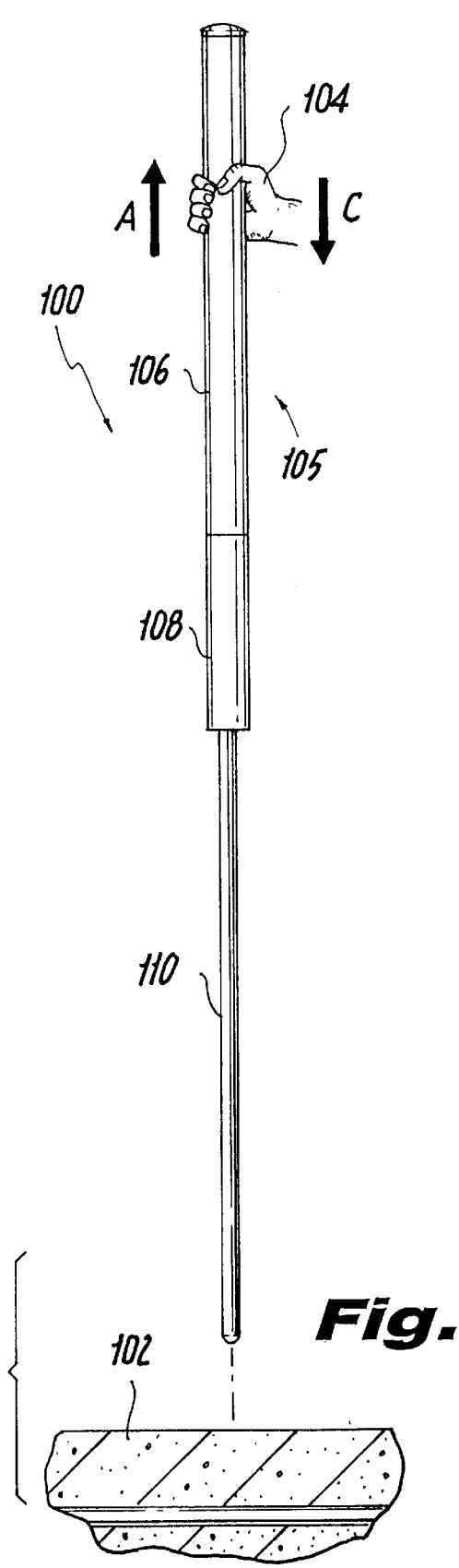
FIG. 2 is a perspective view of an embodiment of the plunger bar held by a hand of an operator above an intended penetration site.

In accordance with the present disclosure, referring now in detail to the drawings wherein like reference numerals identify similar or like components throughout the several views, FIG. 2 describes a plunger bar 100 which reduces the impact shock to an operator. Plunger bar 100 reduces the impact forces through the use of a spring damper system, described hereinbelow. The shock waves caused by the impact of driving plunger bar 100 into the ground are thereby attenuated creating a condition of reduced stress to the operator's arms and wrists.

The preferred embodiment of the plunger bar is capable of attenuating peak shock waves due to impact, for example from approximately 1500 g's to about 500 gas. Further, given the damping arrangement, the initial force imparted to plunger bar 100 is reduced from the prior art, for example 36% less force need be supplied by the operator to cause the same effect.

As shown in FIG. 2, plunger bar 100 is held above an intended penetration site 102 by a hand 104 of an operator. Plunger bar 100 is illustrated with a two-piece barrel 105 having a proximal portion 106 and a distal portion 108. As used herein, the term "proximal" refers to that portion or end which is furthest from the intended penetration site, and the term "distal" refers to that portion or end which is closest to the intended penetration site. Since plunger bar 100 is manually operated, barrel 105 is preferably sized to accommodate the human hand. The preferred shape of barrel 105 is cylindrical. It is envisioned that the weight of barrel 105 may be varied according to an intended application. An optimal weight will create holes as well as allow the efficient use of plunger bar 100 by the operator. Probe 110 is illustrated extending from the distal end of barrel 105 toward the intended penetration site 102. Thus, the operator's hand 104 is moved distally, as indicated by arrow C, to move barrel 105 distally and thereby force probe 110 to penetrate the intended penetration site 102.

Figure 3:
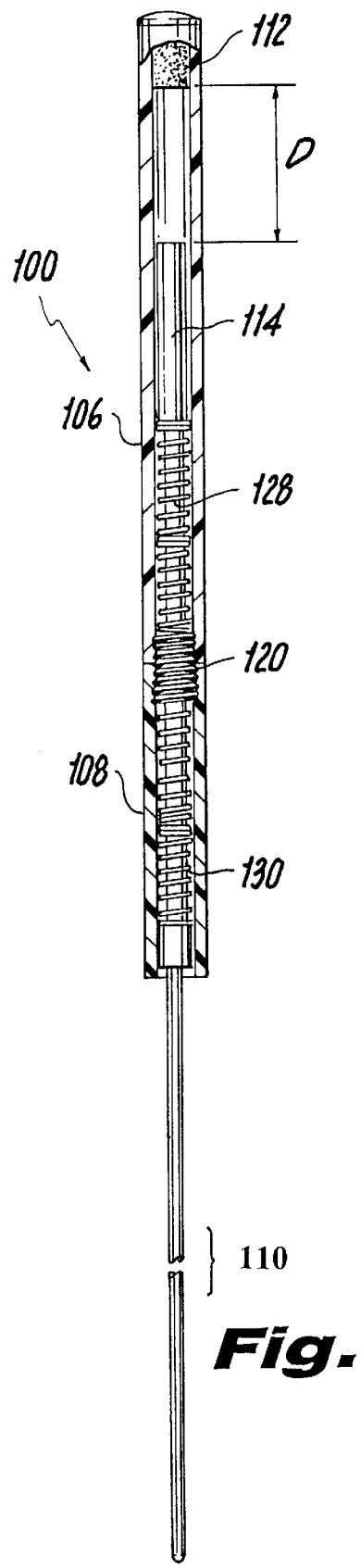
FIG. 3 is a side view in partial cross-section of an embodiment of a plunger bar.

As illustrated in the cross-sectional view of FIG. 3, one preferred embodiment of the spring damper arrangement of the present disclosure includes a gap D provided between a bumper 112 and a proximal end of a hammer mechanism 114. Bumper 112 is preferably constructed of a compressible material, such as neoprene or other resilient, rubber material. When the operator lifts the device in a proximal direction, plunger bar probe 110 slides within hollow cylindrical portion 124 (as will be described below) so that the proximal end of probe 110 separates and is spaced from a distal end of hammer mechanism 114 within portion 124. As the operator moves a barrel 105 distally, momentum is acquired prior to hammer 114 striking the proximal end of probe 110. As hammer 114 strikes probe 110, probe 110 is driven into penetration site 102. The downward impact force is attenuated by springs 128 and 130, and the blow of hammer 114 is softened by bumper 112 creating the damping effect that reduces the stress on the operator's arms and wrists. The individual components of plunger bar 100 will be described with reference to the exploded perspective view shown in FIG. 4.

Figure 4:
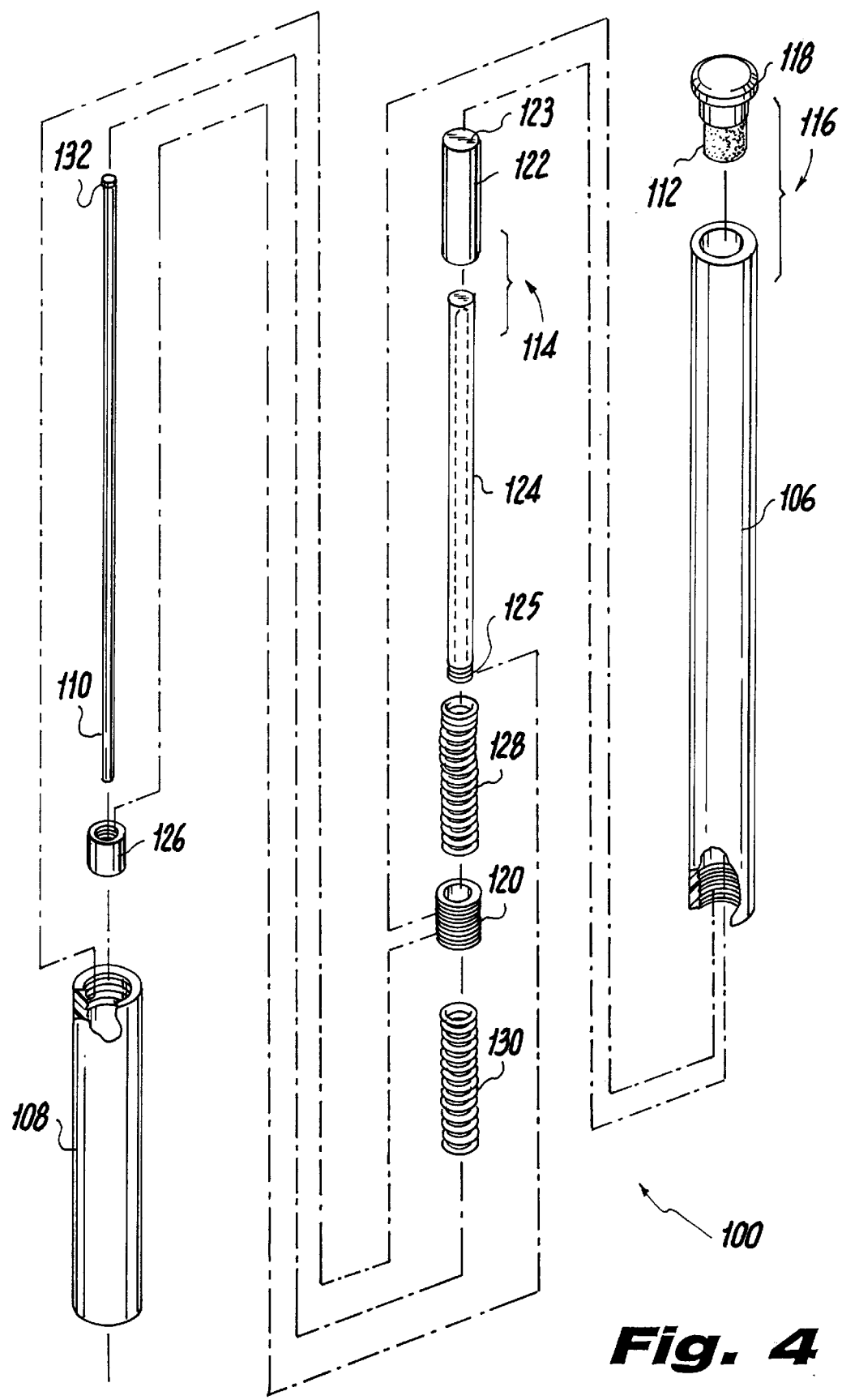
FIG. 4 is an exploded perspective view of an embodiment of a plunger bar.

Referring now to FIG. 4, plunger bar 100 is illustrated in an exploded perspective view to show the assembly of the individual components. A proximal end 116 of plunger bar 100 includes an end cap 118 having bumper 112 attached thereto and is fixedly connected to the proximal end of proximal portion 106 of barrel 105. Proximal portion 106 may be threadably connected at a distal end thereof via threaded coupling 120 to a proximal end of distal portion 108, which may also be threadably coupled to coupling 120.

Hammer 114 includes a solid anvil portion 122 attached to a hollow cylindrical portion 124, and an end cap 126 threadably fixed at threaded end 125 to a distal end of cylindrical portion 124. A first spring 128 is configured and dimensioned to be slidably mounted on hollow cylindrical portion 124 between anvil 122 and coupling 120, and a second spring 130 is configured and dimensioned to be slidably mounted on cylindrical portion 124 between coupling 120 and an end cap 126. While mounted on cylindrical portion 124, spring 128 is restrained from axial movement on its proximal end by anvil 122 and on its distal end by coupling 120. Similarly, second spring 130 is restrained from axial movement on its proximal end by coupling 120 and on its distal end by end cap 126. End cap 126 has a longitudinal bore therethrough dimensioned to insertably receive probe 110. Probe 110 is further received within a longitudinal bore formed within cylindrical portion 124. A flange 132 is formed on the proximal end of probe 110 to prevent probe 110 from completely sliding out of end cap 126.

In use, as an operator prepares to create a hole with plunger bar 100, a distal tip of probe 110 is positioned on a location for the desired hole. The plunger bar is lifted in the direction of Arrow "A", as seen in FIG. 2, and once the desired height is reached by the operator, barrel 105 is accelerated downward in the direction of Arrow "C" causing anvil 122 of hammer 114 to impact flange 132 of probe 110. Upon impact, probe 110 is driven into the ground. The downward stroke is attenuated by springs 128 and 130. The motion of hammer 114, that is propelled in part by the recoil force of springs 128 and 130, is dampened by bumper 112, which impacts an upper surface 123 of hammer 114. Because the operator holds only barrel 105, the impact shock waves are attenuated through springs 128 and 130 and bumper 112 during the entire impact procedure. Hence, the stress on the arms and wrists of the operator is reduced. Thus, in accordance with the above description of the presently disclosed plunger bar, the impact force which is typically imparted upon the operator is effectively attenuated by both bumper 112 and springs 128 and 130.

It is envisioned that springs 128 and 130 are configured, as shown in the preferred embodiments, with respect to hammer 114 to advantageously provide a system for enhancing the force which is exerted upon plunger 100. That is, the downward motion of bumper 112 and hammer 114 cause spring 130 to compress between coupling 120 and end cap 126. Since coupling 120 is, at least momentarily, held in a fixed position by the hand of the human operator, at least a portion of the recoil force exerted by spring 130 will be directed distally against end cap 126. The spring force exerted on end cap 126 will be transferred through cylindrical portion 124 to anvil 122 which is in contact with the proximal end of probe 110. Hence, the force exerted by hammer 114 on probe 110 will be increased. Therefore, the operator will experience less fatigue and will more effectively drive plunger 100 into the ground, while exerting the same force which was required by conventional plunger bars.

Thus, in accordance with the apparatus as described above, a plunger bar is provided which reduces the fatigue and stress to the operator which results from the impact forces associated therewith, and also increases the penetration force of probe 110.

Figure 5:
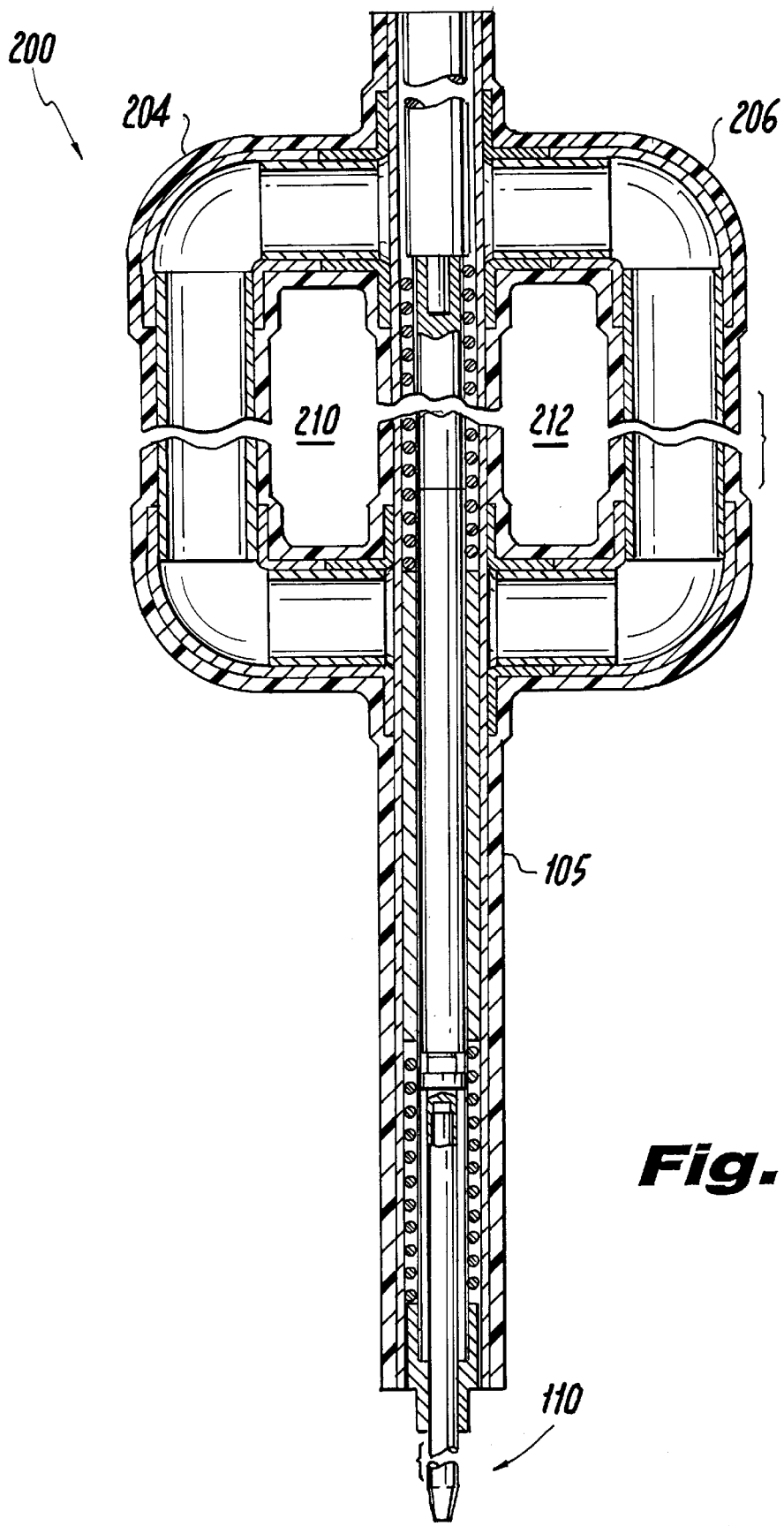
FIG. 5 is a cross-sectional view, in-part elevation, of an alternate embodiment of the present disclosure.

In another embodiment, barrel 105 includes a handle assembly 200, facilitating manual operation of plunger 100. As shown in FIG. 5, handle 200 includes a first handle portion 204 and a second handle portion 206. In the embodiment shown, both handle portions 204 and 206 extend from barrel 105 defining open regions 210 and 212, respectively. Open region 210 and 212 provide sufficient area for an operator to grip handle portions 204 and 206 with his or her hand(s).

Figure 6:
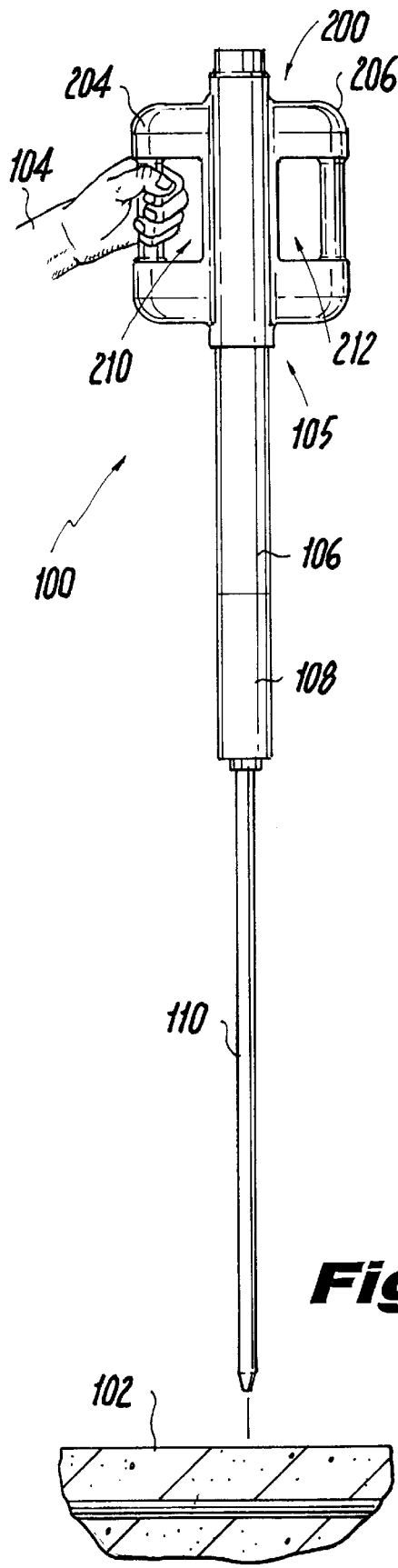
FIG. 6 is another embodiment of the plunger bar held by an operator.
Figure 7:
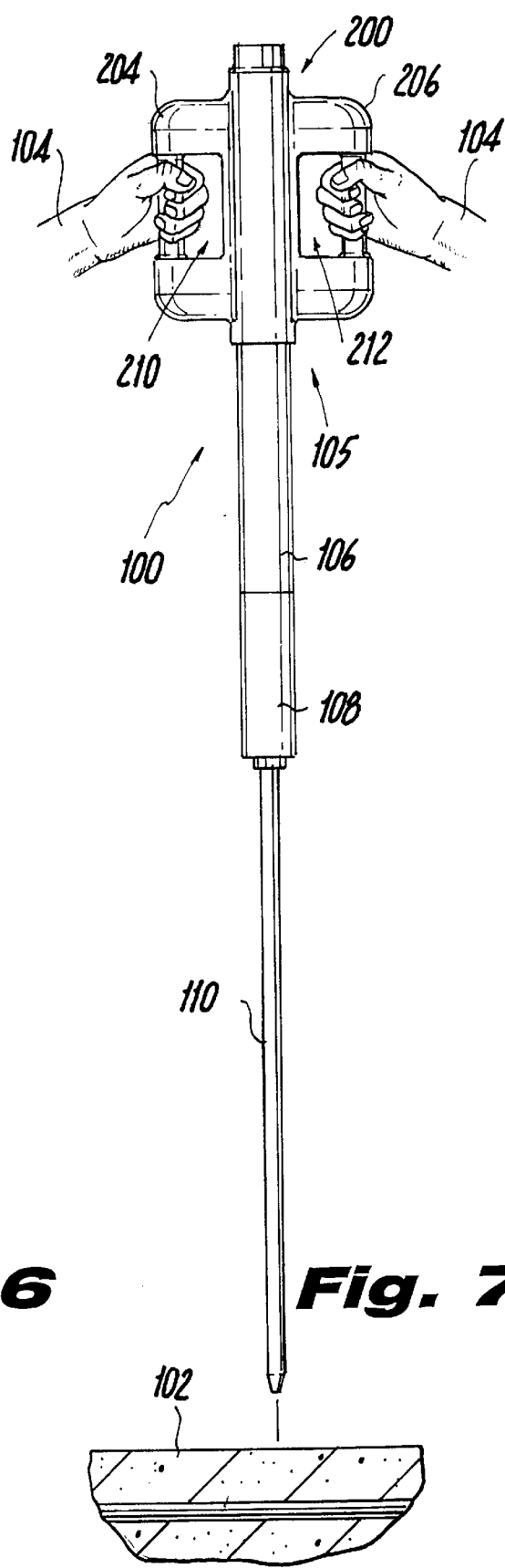
FIG. 7 is yet another embodiment of the plunger bar held by an operator.

In use, as shown in FIG. 6, an operator may grip an individual handle portion, 204 or 206, for operating and manipulating plunger 100 as described hereinabove. Here, operator hand 104 grips handle portion 204. Alternatively, as shown in FIG. 7, an operator may grip handle portion 204 and 206 simultaneously with both hands to exert a greater amount of force and stability while operating plunger 100.

Having described the above embodiments of an improved plunger bar (which are intended to be illustrative and not limiting), it is noted that modifications and variations could be made by those skilled in the art in light of the above teachings. It is therefore to be understood that changes may be made in the particular embodiments which are within the scope and spirit of the disclosure.

What is claimed is:

1. A plunger apparatus for penetrating a surface, the apparatus comprising:

a housing;

a probe configured to penetrate the surface and slidably supported by the housing;

a hammer mechanism slidably supported by the housing and cooperatively engaging the probe to distally advance the probe into the surface; and a damping assembly supported by the housing, the damping assembly including at least one energy absorbing member cooperating with the hammer mechanism to attenuate impact forces generated during the operation of the apparatus.

2. The plunger apparatus according to claim 1, wherein the hammer mechanism includes:

an anvil having a top and a bottom surface, the bottom surface cooperatively engaging the probe to distally advance the probe, a cylinder having a proximal and a distal end, the cylinder fixedly attached to the bottom surface of the anvil at its proximal end and defining a channel therewithin for slidable receipt and support of the probe, and an end cap mounted at the distal end of the cylinder, the end cap defining a distal movable limit for the probe.

3. The plunger apparatus according to claim 1, wherein the damping assembly is positioned within the housing to generate a recoil force for cooperating with the hammer mechanism to increase impact forces for driving the probe into a surface.

4. The plunger apparatus according to claim 3, wherein the damping assembly further includes a second energy absorbing member cooperating with the first energy absorbing member, both members being in operative engagement with the hammer mechanism to attenuate impact forces generated during operation of the apparatus, the second energy absorbing member generating the recoil force to increase impact forces.

5. The plunger apparatus according to claim 2, wherein the energy absorbing member of the damping assembly includes a first energy absorbing member slidably supported about the cylinder and cooperating with the bottom surface of the anvil, a second energy absorbing member slidably supported about the cylinder and cooperating with the end cap.

6. The plunger apparatus according to claim 5, wherein the damping assembly is positioned within the housing whereby the second energy absorbing member generates a recoil force transmitted to the end cap, the recoil force firther transmitted to the cylinder and to the anvil thereby increasing the impact forces for driving the probe into a surface.

7. The plunger apparatus according to claim 1, wherein the damping assembly further includes a bumper member fixedly attached to a proximal portion of the housing, the bumper member cooperating with the hammer mechanism to attenuate impact forces generated during operation of the apparatus.

8. The plunger apparatus according to claim 1, wherein the at least one energy absorbing member comprises a spring assembly.

9. The plunger apparatus according to claim 6, wherein the first and second energy absorbing members are springs.

10. The plunger apparatus according to claim 1, wherein the probe has an increased diameter portion adjacent a proximal end thereof for retaining at least a portion of the proximal end of the probe within the housing.

11. The plunger apparatus according to claim 1, wherein the housing includes a handle assembly.

12. The plunger apparatus according to claim 11, wherein the handle assembly comprises a first handle portion and a second handle portion, each portion extending from the housing and defining an open region therebetween.

13. A plunger apparatus, comprising:

a housing having a proximal portion and a distal portion and defining a channel therewithin;

an elongated probe configured to penetrate a surface and slidably mounted within the housing and axially extending from the distal portion of the housing;

a hammer mechanism cooperatively engageable with a proximal end of the elongated probe, the hammer mechanism including an anvil and a cylinder mounted within the housing, the cylinder fixedly attached to the anvil and defining a channel for supporting the elongated probe therewithin, the anvil being slidably movable within the housing and into engagement with the elongated robe for driving the elongated probe into the surface; and a spring assembly mounted within the housing and slidable about the cylinder and engageable with the anvil, the spring assembly operatively associated with the hammer mechanism to attenuate impact forces generated during operation of the apparatus to a user.

14. The plunger apparatus according to claim 13, wherein the spring assembly is positioned within the housing to increase a driving force for driving the probe into a surface, whereby a first spring generates a recoil force due to engagement with the hammer mechanism, the recoil force generated increasing the impact forces generated, and the first spring and a second spring cooperating with the hammer mechanism to attenuate impact forces generated during operation of the apparatus.

15. The plunger apparatus according to claim 13, wherein the elongated probe has an increased diameter portion adjacent a proximal end thereof for retaining at least a portion of the proximal end of the probe within the housing.

16. A method for detecting gas leaks, comprising the steps of:

positioning a plunger apparatus adjacent to a gas line, the plunger apparatus including: a housing, a probe, a hammer and a damping assembly;

raising the housing of the plunger apparatus to a desired height over a surface adjacent to the gas line; and lowering the housing to accelerate the hammer to impact the probe of the plunger apparatus towards and into the surface for detecting a gas leak.

17. The method according to claim 16, wherein the steps of raising and lowering are consecutively performed for multiple iterations sufficient to detect a gas line below the surface.

* * * * *